United States Patent [19]
Rawls et al.

[11] Patent Number: 5,547,439
[45] Date of Patent: Aug. 20, 1996

[54] EXERCISE SYSTEM

[75] Inventors: R. Lee Rawls, Woodinville; Steven J. Wierlo, Kent; Cathy L. Wade, Monroe, all of Wash.

[73] Assignee: StairMaster Sports/Medical Products, Inc., Kirkland, Wash.

[21] Appl. No.: 216,007

[22] Filed: Mar. 22, 1994

[51] Int. Cl.⁶ ........................................... A63B 21/00
[52] U.S. Cl. ............... 482/5; 482/3; 482/8; 482/900; 482/902
[58] Field of Search ................ 482/1–9, 51, 52, 482/61, 54, 57, 63, 73, 900–902; 434/61, 247

[56] References Cited

U.S. PATENT DOCUMENTS

| | | |
|---|---|---|
| 3,454,942 | 7/1969 | Chamberlin, Jr. et al. |
| 4,358,105 | 11/1982 | Sweeney, Jr. |
| 4,408,183 | 10/1983 | Wills. |
| 4,708,338 | 11/1987 | Potts. |
| 4,919,416 | 4/1990 | DeCloux ............................. 482/901 X |
| 5,089,960 | 2/1992 | Sweeneg, Jr. ............................. 434/61 |
| 5,240,417 | 8/1993 | Smithson et al. ...................... 482/57 X |
| 5,466,200 | 11/1995 | Ulrich et al. ............................ 482/1 X |

*Primary Examiner*—Richard J. Apley
*Assistant Examiner*—Glen E. Richman
*Attorney, Agent, or Firm*—Seed and Berry LLP

[57] ABSTRACT

An exercise system using a plurality of exercise cycles with the users applying user exercise force at user exercise speed. The exercise system includes a display displaying user indicators moving along respective paths of travel on the display simulating the movement of cycles therealong. The paths of travel are displayed to simulate the travel of a plurality of cycles racing against each other. The exercise system further includes a display control measuring the exercise speed of the plurality of users applied to their respective exercise cycles, and determining the applied cumulative exercise efforts of the users. The display control also determines a lead user based upon which of the users has the greatest cumulative exercise effort, and determines when the cumulative exercise effort of particular ones of the users are within a preselected range less than the cumulative exercise effort of the lead user. While the cumulative exercise effort of the particular users remains within the preselected range and in response thereto, the display control adjusts upward the cumulative exercise effort of the particular users by predetermined amounts. The display control controls movement of the user indicators along their respective paths of travel on the display, with the displayed movement of the user indicators along their respective paths of travel being indicative of their respective adjusted cumulative exercise efforts. The user indicators of the particular users are caused to travel along their respective paths of travel in a manner corresponding to the upwardly adjusted exercise efforts of the particular users, thereby giving the particular users an advantage over the lead user.

61 Claims, 3 Drawing Sheets

EXERCISE SYSTEM

TECHNICAL FIELD

The present invention relates generally to exercise equipment, and more particularly, to an exercise system which simulates riders of stationary exercise cycles and other exercise apparatus racing and achieving the benefit of one exerciser drafting behind the other.

BACKGROUND OF THE INVENTION

Stationary exercise cycles and other exercise apparatus such as kayak and rowing machines are well known and a popular way of achieving cardiovascular exercise and strengthening leg and other muscles. However, riding a stationary exercise cycle for a prolonged period of time can cause some users to lose interest in the exercise. To avoid a monotonous exercise routine, conventional exercise cycles include programming which allows the user to select a preprogrammed exercise pattern or a pattern that is determined on a somewhat random basis. One such exercise cycle is described in U.S. Pat. No. 4,358,105. Although these exercise programs do provide the user with some variety in the exercise routine, they still risk losing the interest of the user, at least to some degree.

It will therefore be appreciated that there has long been a significant need for an exercise system using stationary exercise cycles and other exercise apparatus to retain the interest of the users, and to make what can otherwise become a tedious exercise routine more fun. The present invention fulfills these needs and further provides other related advantages.

SUMMARY OF THE INVENTION

The present invention resides in an exercise system having a first exercise apparatus for a first user to apply a first user exercise effort, and a second exercise apparatus for a second user to apply a second exercise effort. The system further includes a display control measuring the exercise efforts of the first and second users applied to the first and second exercise apparatus and determining the cumulative exercise effort for each of the first and second users. The display control determines when the cumulative exercise effort of one of the first and second users is within a preselected range less than the cumulative exercise effort of the other of the first and second users. While the cumulative exercise effort of the one user remains within the preselected range and in response thereto, the display control adjusts the cumulative exercise effort of the one user relative to the cumulative exercise effort of the other user to give the one user an advantage over the other user. The exercise system further includes a display displaying an indication of the relative adjusted cumulative exercise efforts of the first and second users.

In the illustrated embodiment of the invention, the first and second exercise apparatus are first and second exercise cycles. Further, the display displays a first user indicator moving along a path of travel on the display simulating the movement of a first cycle therealong, and a second user indicator moving along a second path of travel on the display simulating the movement of a second cycle therealong. The first and second paths of travel are displayed on the display to simulate the travel of two cycles racing each other.

In the illustrated embodiment of the exercise system, the display control measures the exercise speed of the first and second users applied to the first and second exercise cycles, and determines the cumulative exercise efforts of the first and second users applied to the first and second exercise cycles. The display control further determines when the cumulative exercise effort of one of the first and second users is within a preselected range less than the cumulative exercise effort of the other of the first and second users, and while the cumulative exercise effort of the one user remains within the preselected range and in response thereto, adjusts upward the cumulative exercise effort of the one user by a predetermined amount. The display control controls movement of the first and second indicators along the first and second paths of travel of the display, with the displayed movement of the first user indicator along the first path of travel being indicative of the first user adjusted cumulative exercise effort, and with the displayed movement of the second user indicator along the second path of travel being indicative of the second user adjusted cumulative exercise effort. In such fashion, the corresponding first or second user indicator of the one user is cause to travel along the corresponding first or second path of travel at a rate corresponding to the upwardly adjusted exercise effort of the one user, thereby simulating the one user drafting behind the other user.

In the illustrated embodiment of the invention, the display control adjusts the cumulative exercise effort of the one user upward by a first predetermined amount if within a first subrange of values of the preselected range and by a second predetermined amount less than the first predetermined amount if within a second subrange of values of the preselected range. The second subrange of values being greater in numerical value than the first subrange of values, whereby the one user receives a greater upward adjustment of the cumulative exercise effort when within the preselected range if within the first subrange of values corresponding to a smaller difference between the cumulative exercise efforts of the first and second users.

In the illustrated embodiment, the display control adjusts upward the cumulative exercise effort of the one user by adjusting upward the measured exercise speed of the one user used to determined the cumulative exercise effort of the one user. The display control adjusts upward the measured exercise speed of the one user by a preselected portion of the measured exercise speed of the one user. In the illustrated embodiment, the display control determines the cumulative exercise effort of the first and second user during an exercise period by determining a current incremental exercise effort of the corresponding first or second user during a current time interval and sums the determined current incremental exercise effort with all previously determined incremental exercise efforts during the exercise period.

In an alternative embodiment of the invention, the first and second exercise cycles each include a pair of pedals, and a resistance member applying a variable resistance to the pedals to resist movement of the pedals. Further, the exercise cycle includes a resistance control adjustably controlling the resistance of the resistance member. The resistance control reduces the resistance the resistance member applies the pedals of the corresponding one or second exercise cycle of the first user while the cumulative exercise effort of the one user is being adjusted upward.

In the illustrated embodiment of the invention, the exercise system can accommodate three or more exercise apparatus all displayed by user indicators moving along their respective paths of travel on the display simulating movement of the three or more users therealong. The display control determines a lead user based upon which of the users has the greatest cumulative exercise effort, and determines when the cumulative exercise effort of particular ones of the users are within a preselected range less than the cumulative exercise effort of the lead user. While the cumulative exercise effort of the particular users remains within the preselected range and in response thereto, the display control adjusts upward the cumulative exercise effort of the particular users by a predetermined amount.

In an alternative embodiment of the invention, the exercise system utilizes a simulation generator generating a progressively increasing cumulative exercise effort simulating a second user exercising on a second exercise apparatus. With this embodiment, a human first user of a first exercise apparatus is compared to the simulation generator generated simulated second user and the cumulative exercise effort of the human first user is compared to a generated second user cumulative exercise effort of the simulated second user to determine when the human first user receives an adjustment of the first user's cumulative exercise effort relative to the generated second user cumulative exercise effort.

Other features and advantages of the invention will become apparent from the following detailed description, taken in conjunction with the accompanying drawings.

DETAILED DESCRIPTION OF THE INVENTION

Figure 1:
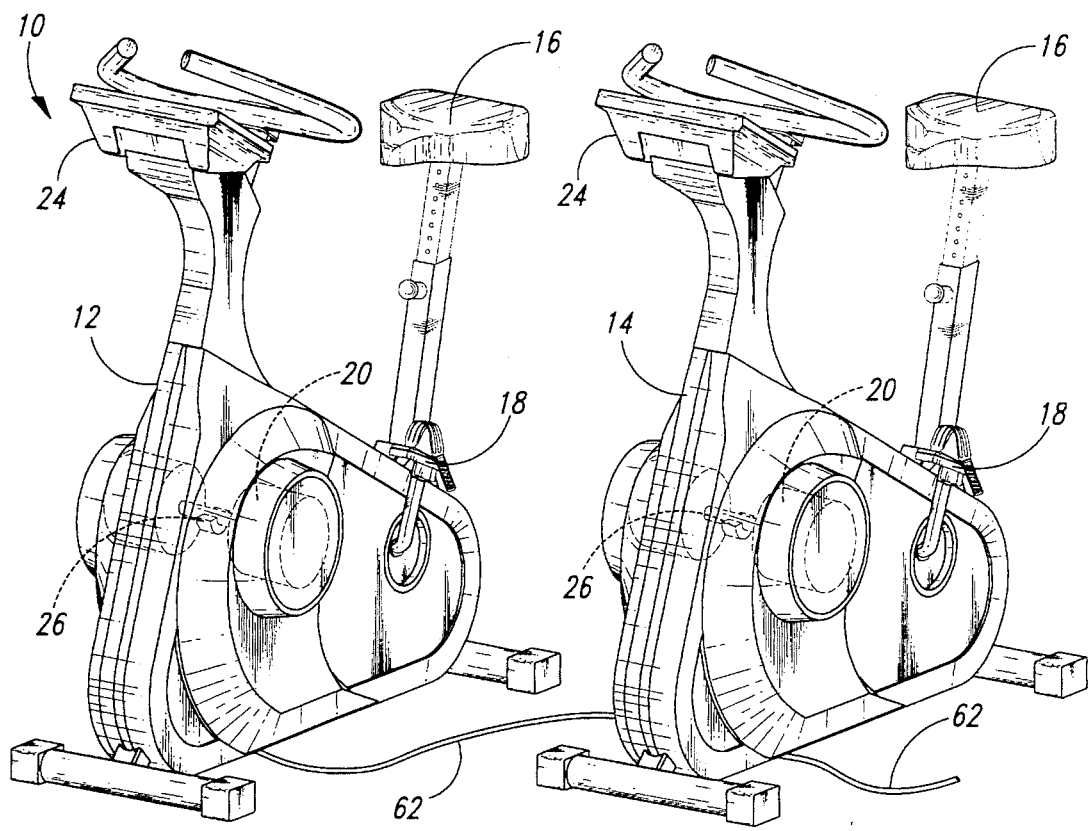
FIG. 1 is a front isometric view of two stationary exercise cycles utilizing the exercise system of the present invention.

As shown in the drawings for purposes of illustration, the present invention is embodied in an exercise system 10 which includes a plurality of stationary exercise cycles, each ridden by an individual user. The exercise system 10 illustrated in FIG. 1 includes a first exercise cycle 12 and a second exercise cycle 14 to which the respective riders thereof apply a selected exercise force at a selected speed. It should be understood that the exercise system 10 may be practiced using additional exercise cycles or other exercise apparatus. The exercise system 10 of the illustrated embodiment of the present invention is constructed to accommodate five exercise cycles.

Figure 2:
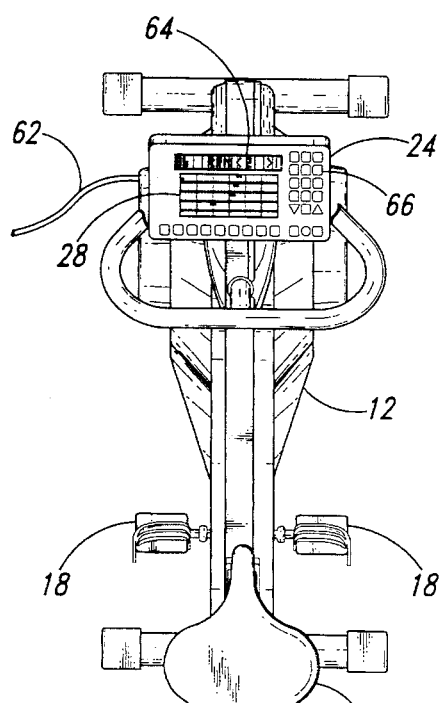
FIG. 2 is a top plan view of one of the exercise cycles of FIG. 1.

As shown in FIGS. 1 and 2, each of the exercise cycles 12 and 14 includes a seat 16 upon which a user sits while placing the user's feet on a pair of conventional pedals 18 which can be rotated by the user's feet, much in the way of peddling a bicycle. A resistance mechanism applies a selectively variable resistance to the pedals to resist movement of the pedals and provide exercise to the user. In the embodiment of the exercise cycles 12 and 14 shown in FIGS. 1 and 2, the resistance mechanism is a conventional fan brake 20 comprising a squirrel cage fan which is turned as a result of the user rotating the pedals 18 and the resistance is provided by the fan encountering air resistance. In an alternative embodiment of the exercise cycle illustrated in FIG. 6, the resistance mechanism is a dynamic brake which may take the form of an alternator or any other well-known dynamic brake mechanism to provide the necessary resistance to the pedals 18. A conventional alternator resistance mechanism is shown and described in U.S. Pat. No. 4,358,105. Another conventional alternator resistance mechanism is shown and described in U.S. Pat. No. 4,708,338. Both U.S. Pat. Nos. 4,358,105 and 4,708,338 are incorporated herein by reference, particularly the portions thereof illustrating and describing the pedal and resistance mechanisms utilized. Other conventional resistance mechanisms such as a friction belt and wheel may be used to provide resistance to the pedals 18.

Figure 6:
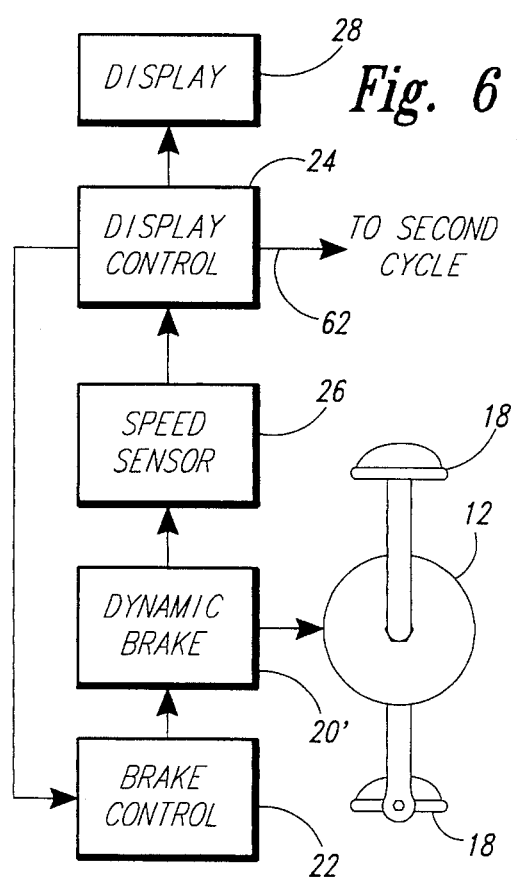
FIG. 6 is a block diagram of an alternative embodiment of one exercise cycle usable with the exercise system of the present invention.

Referring to FIG. 6 by way of example, the dynamic brake 20' is controlled by a brake control 22 which controls the amount of the resistance the dynamic brake applies to the pedals 18. As will be described in detail below, during certain portions of an exercise, it is desirable to adjust the resistance the dynamic brake 20' applies to the pedals 18.

The exercise system 10 of the present invention utilizes the competitive nature of humans to help maintain the interest of the users of the exercise cycles 12 and 14 while they exercise. This is done by simulating a race between the exercise cycles and displaying the race as it progresses on a display 24 mounted on each of the first and second exercise cycles 12 and 14 for viewing by the user riding the exercise cycle. It is noted that while the exercise system 10 is described as using a separate display for each exercise cycle, a single display viewable by the users of all of the exercise cycles may be used in lieu of the individual displays or in addition to the individual displays.

To raise the interest level of the users, not only does the exercise system 10 of the present invention simulate a race between the exercise cycles, but it also simulates the users being able to draft behind each other if the users behind the lead user have expended sufficient cumulative exercise effort to have advanced along an imaginary race course to be within a prescribed distance of the lead user.

Since the exercise cycles 12 and 14 are stationary, the relative positions of the users along the imaginary race course cannot be determined by measuring the distance actually traversed by the exercise cycles. However, an equivalent distance or position along the imaginary race course can be determined by determining the cumulative exercise effort of each of the users of the first and second exercise cycles 12 and 14. Assuming the simulated race course is the same for all users (i.e., has the same flat and hilly areas), the cumulative exercise effort that would be required for each user to traverse the entire imaginary race course can be calculated. By measuring the elapsed time since the beginning of the race and the exercise effort expended by each of the users during the elapsed time, the imaginary progress of the users along the imaginary race course can be calculated. The particular position of a user at any time prior to expending the total exercise effort required to traverse the entire imaginary race course is easily determined by comparing the cumulative exercise effort of the user to the total calculated required exercise effort. If a flat terrain is assumed, a user progresses along the imaginary race course in direct proportion to the cumulative exercise energy expended by the user compared to the total calculated required exercise effort. In other words, each point along the imaginary race course requires the user to expend a specific amount of cumulative exercise effort. If a more complicated terrain is used, a profile can be developed for all positions along the imaginary race course as a function of the cumulative exercise effort required of the user to reach each imaginary position along the race course. This same information is used to determine the separation distance between the users as they progress along the imaginary race course.

The first and second exercise cycles 12 and 14 shown in FIGS. 1 and 2, each provide a known resistance to the pedals 18 that is proportional to the speed of the squirrel cage fan of the resistance mechanism. Hence, the incremental exercise effort expended by a user and the cumulative exercise effort for the user can be determined by simply measuring the speed at which the exercise cycle is being operated by the user during a current time interval. To do this, each cycle has a speed sensor 26 which measures the speed at which the user turns the pedals 18 with the user's feet during the current time interval. Of course, to have a measurable exercise speed, the user of the exercise cycle must apply a sufficient exercise force on the pedals 18 to at least overcome the resistance applied to them by the resistance mechanism 20. By measuring the actual exercise speed, and knowing the speed/resistance relationship of the resistance mechanism, the exercise effort of the user during the current time interval is calculated. The calculated actual exercise effort expended by the user during each current time interval is accumulated as the exercise progresses to produce a cumulative exercise effort for the user. The cumulative exercise effort is periodically updated for each subsequent time interval until the simulated race is over. The cumulative exercise effort is for each user is also converted into the equivalent distance the user would have traveled along the imaginary race course.

Figure 4A:
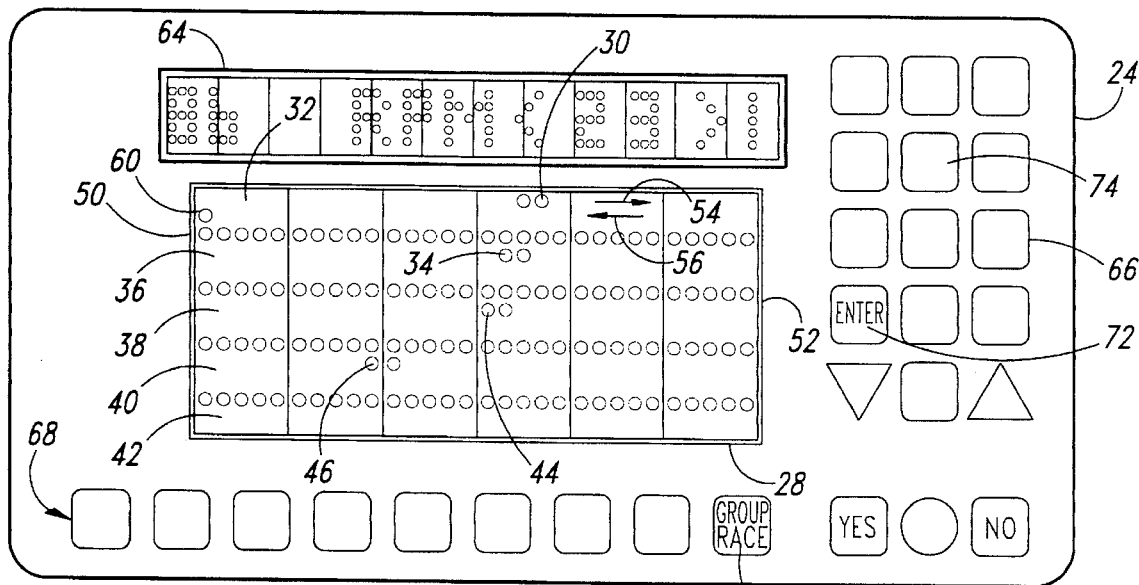
FIG. 4A is an enlarged view of the face portion of the display of FIG. 3 for the first exercise cycle and showing four exercise cycles in a simulated race.

To facilitate maintaining the interest of the users, the display 24 mounted on each of the exercise cycles 12 and 14 has an LED visual display 28 which presents a visual simulation of the imaginary race course and the imaginary travel of the users therealong. As best shown in FIG. 4A, a first user indicator 30 in the form of illuminated LED elements is displayed moving along a simulated first lane 32 to simulate movement of the first exercise cycle 12 along the first lane. Similarly, a second user indicator 34 in the form of illuminated LED elements is displayed moving along a simulated second lane 36 to simulate movement of the second exercise cycle along the second lane. The first and second lanes 32 and 36 are displayed side by side to simulate the travel of two cycles racing each other along the same imaginary race course. As previously noted, the illustrated embodiment of the exercise system 10 is designed to accommodate five exercise cycles engaging in a simulated race. As such, the display 24 also includes a third lane 38, a fourth lane 40, and a fifth lane 42. In FIG. 4A there is also shown a third user indicator 44 in the form of illuminated LEDs in the third lane 38 and a fourth user indicator 46 in the form of illuminated LEDs in the fourth lane 40. No fifth user indicator is shown in the fifth lane 42 in FIG. 4A since it illustrates a race involving only four users riding four stationary exercise cycles.

Because an imaginary race course may be selected which extends over many miles, and the size limitation of the visual display 28, the full imaginary race course cannot be shown on the visual display while still achieving a visual presentation where the user indicators 30, 34, 44 and 46 move at an acceptable speed across the visual display. As such, the visual display 28 only displays a portion of the total imaginary race course. To increase the amount of the imaginary race course which is displayed, each of the lanes 32, 36, 38, 40 and 42, which extend between a left border 50 and a right border 52, includes an upper path in the form of an upper row of LED elements which are selectively illuminated to form the user indicator to show the user indicator moving from the left border 50 to the right border 52 in the direction indicated by arrow 54. Each of the lanes also includes a lower path in the form of an adjacent lower row of LED elements which are selectively illuminated to form the user indicator to show the user indicator moving from the right border 52 to the left border 50 in the direction indicated by arrow 56. The scale of the lanes is selected so that an indicator moving from the left border 50 to the right border 52, and back again to the left border travels the equivalent of one mile along the imaginary race course.

With this arrangement, the user indicator 30, 34, 44 or 46 for a particular user begins adjacent the left border 50 and travels rightward along the upper row of LED elements until it reaches the right border 52, and then travels leftward along the lower row of LED elements until it reaches the left border 50. Assuming that the end of the imaginary race course has not yet been reached, the user indicator continues its movement along the imaginary race course by being displayed once again in the upper row of LED elements and traveling rightward from a position adjacent the left border 50 toward the right border 52. If all of the users participating in the imaginary race expend a generally similar cumulative exercise effort, the user indicators 30, 34, 44 and 46 and the user indicator for the fifth lane 42 which is not shown in FIG. 4A, will travel along the upper and lower rows of LED elements of their respective lanes 32, 36, 38, 40 and 42 in proximity with each other and appear to be traveling along an imaginary race course first from left to right, then from right to left, and then again from left to right. This will continue until a sufficient cumulative exercise effort has been measured for a user to have traversed the full imaginary race course and reached the end of the race.

Figure 4B:
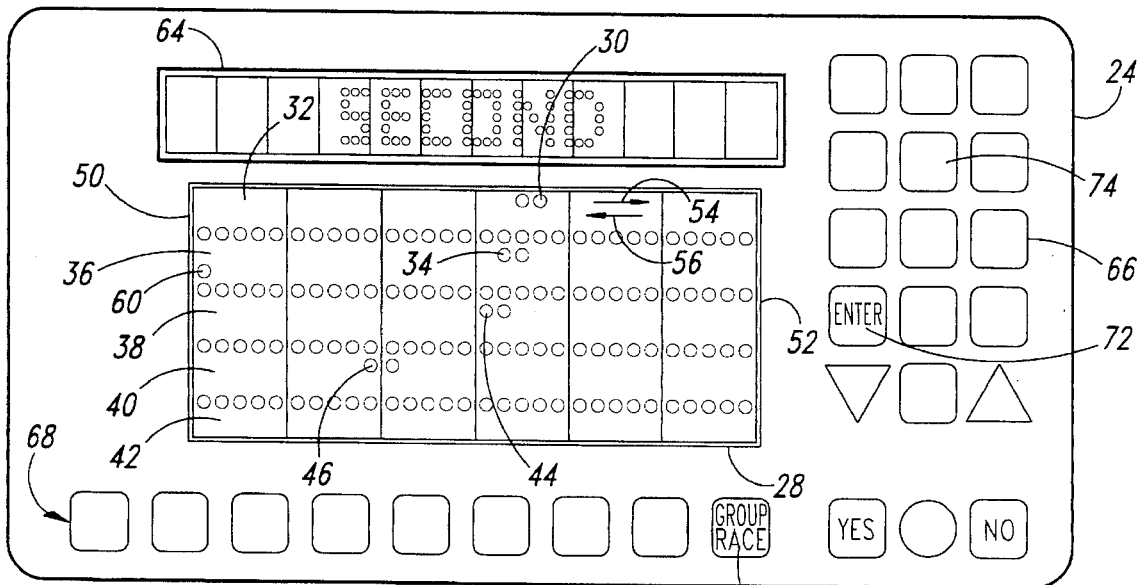
FIG. 4B is another view of the face portion of the display of FIG. 3 but for the second exercise cycle and showing a different display mode and the lane marked for a second user.

The visual display 28 of the display 24 for each of the exercise cycles 12 and 14, as well as the visual displays for the additional three exercise cycles which can be utilized with the illustrated embodiment of the exercise system 10, has an indicator 60 in the form of an illuminated single LED element adjacent the left border 50 in the lane which corresponds to the lane the user on whose exercise cycle the display 24 is mounted. For example, since the display 24 shown in FIG. 4A is mounted on the first exercise cycle 12, the indicator 60 is in the first lane 32 and identifies for the rider of the exercise cycle that the user indicator 30 in the first lane 32 is for the first exercise cycle 12 which that user is riding. The display 24 for the rider of the second cycle 14 is shown in FIG. 4B and has a similar indicator 60 in the second lane 36.

As discussed above, not only does the exercise system 10 of the present invention present on the visual displays 28 the progress of a simulated race along an imaginary race course to increase the interest level of the users, the exercise system also simulates one or more users "drafting" behind another user. To determine which user gets the benefit of drafting, the display 24 contains electronics to perform the necessary computational functions. These electronics do the necessary calculations to determine the cumulative exercise efforts of the users during the course of the race, and control the visual display 28 and other displays which will be discussed below.

Figure 5:
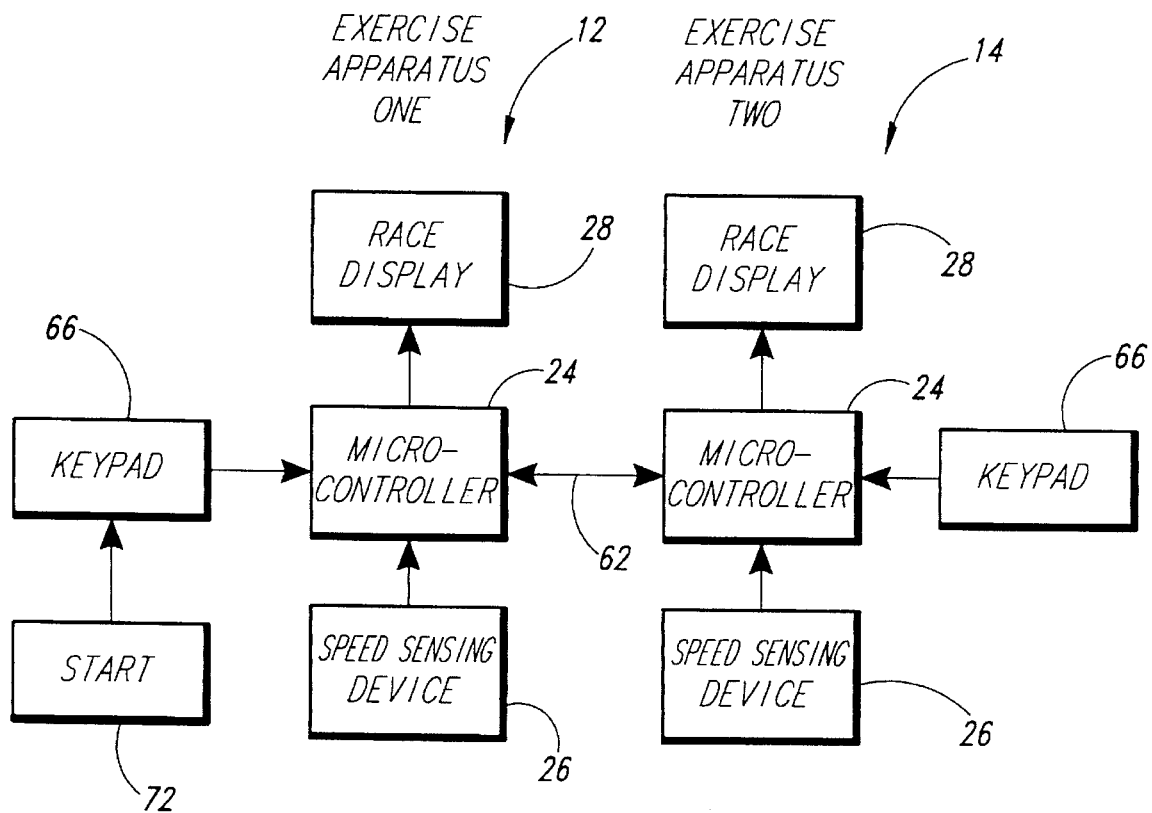
FIG. 5 is a block diagram of the exercise system of FIG. 1.

As shown schematically in FIG. 5, the display 24 includes a microcontroller comprising a microprocessor and associated random access memory (RAM) and read-only memory (ROM) which contains the needed programming for the microprocessor. The microprocessor of the display 24 of each of the exercise cycle 12 and 14 receives a speed indicating signal from the speed sensor 26 which indicates the measured exercise speed that the user of the particular exercise cycle is applying thereto. As described above, from this measured exercise speed for each time interval during the length of the race, the microprocessor determines the cumulative exercise effort of the user of the particular exercise cycle. As also described above, the resistance is proportional to the squirrel cage fan speed so that cumulative exercise effort can be calculated based upon the known resistance for any speed, the measured exercise speed, and the elapsed time during which the exercise speed is maintained.

The microprocessor for the display 24 of each of the first and second exercise cycles 12 and 14, and any of the three additional exercise cycles which can be used with the illustrated embodiment of the exercise system 10, determines the cumulative exercise effort for the particular exercise cycle to which it is mounted. This information is exchanged between the displays 24 of the exercise cycles over a cable 62 which interconnects the displays 24, particularly the microprocessors thereof. This information is used to periodically update the visual display 28 of each display 24 to show the race progress and other information.

By knowing the cumulative exercise effort of all of the exercise cycles, the microprocessor of the display 24 of each exercise cycle can determine when the cumulative exercise effort of one user is within a preselected range less than the cumulative exercise effort of another user who has progressed farther along the imaginary race course. For example, using the race progress illustrated in FIG. 4A, the microprocessor of the display 24 of the first exercise cycle 12 (see user indicator 30) can determine that the second user riding the second exercise cycle 14 (see user indicator 34) has a cumulative exercise effort very close to but less than the cumulative exercise of the first user. In the presently preferred embodiment of the invention, if the cumulative exercise effort of one user is the equivalent of within the range of 176 feet behind another user who has traveled farther along the imaginary race course and is in the lead, the display 24 of each user's exercise cycle will simulate the trailing user drafting behind the lead user for so long as the cumulative exercise effort of the trailing user remains within the preselected equivalent 176-foot range. The actual effect of drafting one bicycle behind another bicycle is simulated when one user is detected as being within the preselected 176-foot range behind a lead user by adjusting upward the calculated cumulated exercise effort of the drafting user by a predetermined amount. While a 176-foot range has been used, any other desired range may be used to determine when the drafting advantage should be given.

In the presently preferred embodiment of the invention, since the resistance for a given speed applied by the brake 20 to the pedals 18 does not change during the exercise, the upward adjustment of the calculated cumulative exercise effort is accomplished by increasing the actual measured speed when calculating the cumulative exercise effort. For example, if the actual measured speed of the drafting user is 100 revolutions per minute (RPM), the speed used to calculate the cumulative exercise effort for the drafting user is adjusted upward by, for example, 6% to be 106 RPMs. In effect, this means that for the same actual exercise effort applied by the drafting user, the drafting user will have the corresponding user indicator on the visual display 28 move along the corresponding lane for that user at an increased rate corresponding to the 6% increase in RPM. If the drafting user were to maintain the same exercise effort, this would relatively quickly result in the drafting user overtaking the lead user and hence losing the benefit of the drafting since the measured speed would no longer be adjusted upward to calculate the cumulative exercise effort. In fact, since the formerly leading user would now be in a drafting position within the preselected 176-foot range of the former drafting user (who is now in the position of the lead user), the former lead user would now get the benefit of drafting.

As noted, while the drafting user may elect to simply maintain the same exercise effort by continuing to move the pedals 18 at the same exercise speed and speed ahead, the drafting user may also elect to maintain the drafting user's position behind the lead user, and hence keep receiving the advantage of drafting for a prolonged period of time. This is done by the drafting user reducing the exercise effort applied to the exercise cycle of the drafting user by a sufficient amount that the drafting user maintains an adjusted cumulative exercise effort less than the cumulative exercise effort of the lead user. As noted above, since the drafting user is achieving a 6% adjustment in the actual measured exercise speed, and hence a corresponding adjustment in the incremental exercise effort used to calculate the cumulative exercise effort for the drafting user, the drafting user must reduce the exercise speed being applied to the exercise cycle being ridden by about 6%. A reduction by less will begin to close the gap between the drafting user and the lead user. The result is that the drafting user will maintain a position behind the lead user and be able to move along the imaginary race course at the same rate as the lead user while applying less exercise effort than the lead user. This simulates the effect of drafting, which in a real bicycle race results in the drafting rider being able to position himself behind the lead rider and input less exercise effort to achieve the same travel along the race course as the lead rider.

Naturally, while the drafting user can maintain this trailing position throughout the balance of the race and have a lower cumulative exercise effort than the lead user, the drafting user will ultimately lose the race. Thus, a strategy must be developed of how to best take advantage of the benefit of drafting but still end up in front of the other users by the end of the race. The competition of being in a race and the race strategy associated therewith help retain the interest of the users, and the ability to take advantage of the benefit of drafting behind a lead user adds a significantly increased requirement for strategy and significantly increases the interest and fun of the users. With the exercise system 10 of the present invention, what might otherwise be a boring exercise routine to some users becomes a challenging and fun competitive activity paralleling the sport of bicycle racing. As noted above, these same advantages can be achieved by utilizing the invention in other exercise apparatus such as kayak and rowing machines.

In the illustrated preferred embodiment of the invention, the preselected range used when comparing the adjusted cumulative exercise efforts of the users to determine if one receives the benefit of drafting is divided into two subranges. In particular, when comparing the adjusted cumulative exercise effort of a trailing user to a lead user, if the trailing user is within the equivalent of 88 feet behind the lead user, the trailing user will get the 6% advantage discussed above. However, if the trailing user is within the subrange of between 88 to 176 feet behind the lead user, the advantage will only be 3%.

In an actual bicycle race, several riders can be bunched together behind a lead rider and all achieve some benefit of drafting. In the presently preferred embodiment of the invention, if a second user is positioned within the equivalent of a 176 foot-range of the lead user, but behind the first drafting user, the second user will also receive the benefit of drafting. In fact, if the second drafting user in the group is within the equivalent of 88 feet behind the lead user, the second drafting user receives a 7% advantage. If the second drafting user is within the subrange of between 88 to 176 feet behind the lead user, the second trailing user receives only a 4% advantage. This describes a three-user group all within the equivalent 176 feet of the lead user as is illustrated on the visual display of FIG. 4A. If the order of the drafting users should change, the advantage given will similarly change. Also, if any one of the drafting riders falls more than the equivalent of 176 feet behind the lead user, that user will no longer receive any drafting advantage.

The same situation can occur with a group of four or five users in close proximity. In the case of a four-user group, the third drafting user in the group will receive a 5% advantage if within the subrange of 88 feet behind the lead user (and behind all 3 other users also), and a 2% advantage if within the subrange of between 88 to 176 feet behind the lead user. In a five-user group, the fourth drafting user receives a 2% advantage if within the subrange of 88 feet behind the lead user (and behind all four other users also), and only a 1% advantage if within the subrange of between 88 to 176 feet behind the lead user. As mentioned above, in the event one of the drafting users falls more than equivalent 176 feet behind the lead user, no further drafting advantage is given and the calculated exercise effort for the user is based upon the actual measured exercise speed without any upward adjustment. Since the adjusted cumulative effort included all previous adjustments resulting from drafting at various times during the course of the simulated race, the user's position along the imaginary race course does reflect the advantage previously realized from drafting.

In the visual display 28 of FIGS. 4A and 4B, the fourth user indicated by the fourth user indicator 46 in the fourth lane 40 is shown as being greater than the equivalent 176-foot range behind the lead user 30, and hence as getting no drafting advantage. It is noted that while there may be one user that is the equivalent of greater than 176 feet in front of all of the other users, some or all of the other users may be grouped within the equivalent 176 feet of another user who is then considered the lead user and those following this lead user will receive the advantages discussed above based upon their position within the group. It is possible that with five users there may be a maximum of two drafting groups (e.g., a first lead user with two drafting users and a second lead user with three drafting users), and the members of each group receive a drafting advantage based on their position relative to the lead user of that group. As few as two and as many as all five users may be in the same drafting group.

In the presently preferred embodiment of the exercise system 10, the display 24 also includes a second visual display 64 in the form of multiple rows of LED elements which are controlled by the microprocessor of the display 24 to display various information to the user of the exercise machine on which the display 24 is mounted much like provided by a reader board. This includes a numerical indication of the exercise speed expressed in revolutions per minute (RPM) of the user riding the exercise cycle on which the display 24 is mounted. This is indicated as 86 RPM in the display of FIG. 4A. The second visual display 64 further displays a numerical indication of the calculated cumulative exercise effort of the user, including the adjustments made when gaining the advantage of drafting, in the form of the number of laps remaining in the race. In the display of FIG. 4A this is indicated to be one lap (a lap being a travel of the user indicator from the left border 50 to the tight border 52 and back to the left border—the equivalent of one mile). The second visual display 64 also displays a statement of which of the users is within the preselected equivalent 176-foot range of the lead user and is therefore obtaining the advantage of drafting. This is indicated as the second and third users in the display of FIG. 4A by the user numbers between the <> marks. This is displayed for only as long as these users remain in the position of drafting users.

Figure 3:
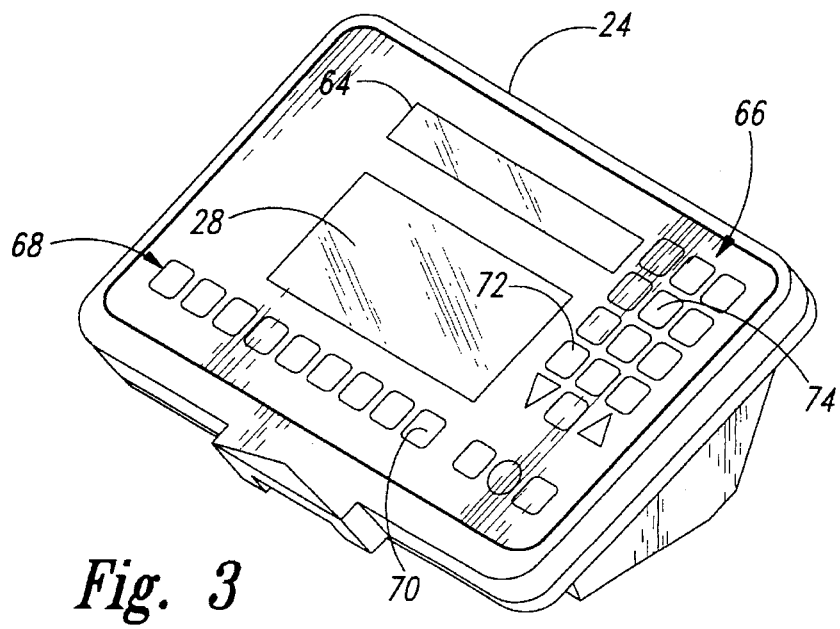
FIG. 3 is an enlarged, isometric view of the display used with each of the exercise cycles of FIG. 1.

As can best be seen in FIGS. 3, 4A, and 4B, the display 24 includes a keypad 66 by which information can be input to the display control 24 and operation of the exercise cycle can be controlled. The display 24 also includes a row of buttons 68, one of which being a "GROUP RACE" button 70 used to select the mode of operation for the exercise cycle described above which has a plurality of users on different exercise cycles entered in a simulated race over an imaginary race course. A start button 72, which consists of the "ENTER" button of the keypad 66, serves as a start button which one of the users in the simulated race can press to commence the race. The visual display 28 is controlled by determining the cumulative exercise efforts of the users commencing upon the activation of the start button 70.

Another button 74 of the keypad 66 is used to alter the information display of the second visual display 64. As shown in FIG. 4B, when the button 74 is pressed the second visual display 64 states the position in the simulated race of the user of the exercise cycle on which the display 24 is mounted. For the display 24 of FIG. 4B, which is mounted on the second exercise cycle 14, the second user is indicated as being in second position by the word "SECOND".

In the embodiment of the exercise cycle of FIG. 6 when used in the exercise system 10 of the present invention, the brake control 22 is used to reduce the resistance the dynamic brake 20' applies to the pedals 18 of any one of the exercise cycles with a rider in the position with respect to the other users to receive the advantage of drafting. In other words, during the portion of the exercise routine when the user is determined to be a drafting user, and the cumulative exercise effort of the drafting user is being adjusted upward, the brake control 22 controls the dynamic brake 20' to reduce the resistance the dynamic brake applies to the pedals 18. In such fashion, the drafting user can elect to either continue inputting the same exercise effort by increasing the rate the pedals 18 are being turned and thereby begin to close the gap with the lead user, or continue turning the pedals at about the same speed and maintain approximately the same cumulative exercise effort as the lead user, and hence approximately the same progress along the imaginary race course in a position behind the lead user, even though less actual exercise effort is required on the part of the drafting user to do so because of the reduced resistance to the pedals.

This embodiment of the exercise cycle provides an experience of drafting behind a rider where the reduced wind resistance resulting from being behind the lead rider allows the drafting rider to pedal at the same speed to keep the bicycle traveling at the same speed as the lead rider, but encounter less resistance and require less exercise effort be expended to maintain the position behind the lead rider.

It is noted that while the presently preferred embodiment of the exercise system 10 adjusts the cumulative exercise effort of the drafting user upward to simulate the drafting of a trailing user behind a lead user, a similar effect can be achieved by not adjusting upward the cumulative exercise effort of the drafting user but rather by adjusting downward the cumulative exercise effort of the lead user. Since this would likely result in an impression on the part of the users that the lead user was being penalized as a result of the drafting, rather than the drafting users being advantaged, this approach is not believed as desirable to users.

The exercise system 10 of the present invention may also be constructed with the microprocessor of the display 24 generating a simulated rider with the human users being able to race against the computer generated rider. This would be particularly handy where a person wishes to achieve the benefits of the present invention but no other persons are available who wish to engage in a simulated race, or a person wishes to utilize the present invention by himself or herself. The microprocessor of the display 24 generates a progressively increasing cumulative exercise effort simulating a second user exercising on a second exercise cycle while a human first user exercises on a first exercise cycle. This can be a simple preprogrammed exercise pattern for the simulated second user (for example, an average constant exercise effort which accumulates equally throughout the race as if the simulated user was operating the imaginary second exercise cycle at a constant preselected speed), or a more intelligent program which incorporates competitive logic such as is well known in computerized chess game programs. Other than calculating the simulated second user's cumulative exercise effort expended along the imaginary race course rather than measuring it, the exercise system 10 functions as described above to determine when the human first user will receive the advantage of drafting and the amount of the advantage received. If desired, the simulated second user may also achieve the advantage of drafting when within the equivalent 176-foot range behind the human first user.

It will be appreciated that, although specific embodiments of the invention have been described herein for purposes of illustration, various modifications may be made without departing from the spirit and scope of the invention. Accordingly, the invention is not limited except as by the appended claims.

We claim:

1. An exercise system, comprising:
    a first exercise cycle for a first user to apply a first user exercise force at a first user exercise speed;
    a second exercise cycle for a second user to apply a second exercise force at a second exercise speed;
    a display displaying a first user indicator moving along a first path of travel on the display simulating the movement of a first cycle therealong, and displaying a second user indicator moving along a second path of travel on the display simulating the movement of a second cycle therealong, the first and second paths of travel being displayed on the display to simulate the travel of two cycles racing each other; and
    a display control measuring the exercise speed of the first and second users applied to the first and second exercise cycles, determining the cumulative exercise efforts of the first and second users applied to the first and second exercise cycles, and determining when the cumulative exercise effort of one of the first and second users is within a preselected range less than the cumulative exercise effort of the other of the first and second users, and while the cumulative exercise effort of the one user remains within the preselected range and in response thereto, adjusting upward the cumulative exercise effort of the one user by a predetermined amount, the display control controlling movement of the first and second indicators along the first and second paths of travel of the display, with the displayed movement of the first user indicator along the first path of travel being indicative of the first user adjusted cumulative exercise effort, and with the displayed movement of the second user indicator along the second path of travel being indicative of the second user adjusted cumulative exercise effort, whereby the corresponding first or second user indicator of the one user is caused to travel along the corresponding first or second path of travel at a rate corresponding to the upwardly adjusted exercise effort of the one user, thereby simulating the one user drafting behind the other user.

2. The exercise system of claim 1 wherein the display includes a first display mounted in association with the first exercise cycle for viewing by the first user and a second display mounted in association with the second exercise cycle for viewing by the second user, and the display control includes a first display control controlling movement of the first and second user indicators on the first display and a second display control controlling movement of the first and second indicators on the second display.

3. The exercise system of claim 2 wherein the first and second displays each define the first path of travel by a displayed first lane with the first user indicator moving along in the first lane and the second path of travel by a displayed second lane with the second user indicator moving along in the second lane.

4. The exercise system of claim 3 wherein the first lane displayed on the first display is marked to identified to the first user the first lane as having the first user indicator, and the second lane displayed on the second display is marked to identify to the second user the second line as having the second user indicator.

5. The exercise system of claim 3 wherein the first and second lanes each extend between spaced apart first and second ends, and each has a first path portion along which the corresponding first or second user indicator travels from the first end to the second end and a second path portion along which the corresponding first or second user indicator travels from the second end to the first end.

6. The exercise system of claim 1 wherein the display further displays a numerical indication of at least one of the first and second exercise speeds.

7. The exercise system of claim 1 wherein the display further displays a numerical indication of the adjusted cumulative exercise efforts of the first and second users.

8. The exercise system of claim 1 wherein the display further displays a statement of which of the first or second users is the one user with an adjusted cumulative exercise effort within the preselected range during the time when the adjusted cumulative exercise effort remain with the preselected range.

9. The exercise system of claim 1 wherein the display further displays a statement of which of the first or second users had the greatest adjusted cumulative exercise effort and which has the lesser adjusted cumulative exercise effort.

10. The exercise system of claim 1 wherein the display control adjusts the cumulative exercise effort of the one user upward by a first predetermined amount if within a first subrange of values of the preselected range and by a second predetermined amount less than the first predetermined amount if within a second subrange of values of the preselected range, with the second subrange of values being greater in numerical value than the first subrange of values, whereby the one user receives a greater upward adjustment of the cumulative exercise effort when within the preselected range if within the first subrange of values corresponding to a smaller difference between the cumulative exercise efforts of the first and second users.

11. The exercise system of claim 1 further including a user activated start selector, and wherein the display control determines the cumulative exercise efforts of the first and second users commencing upon user activation of the start selector.

12. The exercise system of claim 1 wherein each of the first and second exercise cycles includes a pair of pedals, a resistance member applying a variable resistance to the pedals to resist movement of the pedals and a resistance control adjustably controlling the resistance of the resistance member, and wherein the resistance control reduces the resistance the resistance member applies to the pedals of the corresponding first or second exercise cycle of the one user while the cumulative exercise effort of the one user is being adjusted upward.

13. The exercise system of claim 1 wherein the display control adjusts upward the cumulative exercise effort of the one user by adjusting upward the measured exercise speed of the one user used to determine the cumulative exercise effort of the one user.

14. The exercise system of claim 13 wherein the display control adjusts upward the measured exercise speed of the one user by a preselected portion of the measured exercise speed of the one user.

15. The exercise system of claim 1 wherein the display control determines the cumulative exercise effort of the first and second users during an exercise period by determining a current incremental exercise effort of the corresponding first or second user during a current time interval and summing the determined current incremental exercise effort with the previously determined cumulative exercise efforts during the exercise period.

16. The exercise system of claim 15 wherein the display control adjusts upward the cumulative exercise effort of the one user by adjusting upward the determined current incremental exercise effort.

17. The exercise system of claim 16 wherein the display control determines the current incremental exercise effort based on the measured speed of the one user during the current time interval, and adjusts upward the determined current incremental exercise effort by adjusting upward the measured exercise speed of the one user during the current time interval.

18. An exercise system, comprising:

a first exercise cycle for a first user to apply a first user exercise force at a first user exercise speed;

a second exercise cycle for a second user to apply a second exercise force at a second exercise speed;

a display control measuring the exercise speed of the first and second users applied to the first and second exercise cycles, determining the cumulative exercise efforts of the first and second users applied to the first and second exercise cycles, and determining when the cumulative exercise effort of one of the first and second users is within a preselected range less than the cumulative exercise effort of the other of the first and second users, and while the cumulative exercise effort of the one user remains within the preselected range and in response thereto, adjusting upward the cumulative exercise effort of the one user by a predetermined amount; and a display displaying an indication of the relative adjusted cumulative exercise efforts of the first and second users.

19. The exercise system of claim 18 wherein the display control adjusts the cumulative exercise effort of the one user upward by a first predetermined amount if within a first subrange of values of the preselected range and by a second predetermined amount less than the first predetermined amount if within a second subrange of values of the preselected range, with the second subrange of values being greater in numerical value than the first subrange of values, whereby the one user receives a greater upward adjustment of the cumulative exercise effort when within the preselected range if within the first subrange of values corresponding to a smaller difference between the cumulative exercise efforts of the first and second users.

20. The apparatus of claim 18 wherein the display control converts the adjusted cumulative exercise effort of the first and second users into equivalent positions of the first user relative to the second user along a path of travel, and the display displays an indicator for each of the first and second users positioned along the path of travel at its equivalent positions.

21. The exercise system of claim 18 wherein each of the first and second exercise cycles includes a pair of pedals, a resistance member applying a variable resistance to the pedals to resist movement of the pedals and a resistance control adjustably controlling the resistance of the resistance member, and wherein the resistance control reduces the resistance the resistance member applies to the pedals of the corresponding first or second exercise cycle of the one user while the cumulative exercise effort of the one user is being adjusted upward.

22. The exercise system of claim 18 wherein the display control adjusts upward the cumulative exercise effort of the one user by adjusting upward the measured exercise speed of the one user used to determine the cumulative exercise effort of the one user.

23. The exercise system of claim 22 wherein the display control adjusts upward the measured exercise speed of the one user by a preselected portion of the measured exercise speed of the one user.

24. The exercise system of claim 18 wherein the display control determines the cumulative exercise effort of the first and second users during an exercise period by determining a current incremental exercise effort of the corresponding first or second user during a current time interval and summing the determined current incremental exercise effort with the previously determined cumulative exercise efforts during the exercise period.

25. The exercise system of claim 24 wherein the display control adjusts upward the cumulative exercise effort of the one user by adjusting upward the determined current incremental exercise effort.

26. The exercise system of claim 25 wherein the display control determines the current incremental exercise effort based on the measured speed of the one user during the current time interval, and adjusts upward the determined current incremental exercise effort by adjusting upward the measured exercise speed of the one user during the current time interval.

27. An exercise system, comprising:

a first exercise cycle for a first user to apply a first user exercise effort;

a second exercise cycle for a second user to apply a second exercise effort;

a display displaying a first user indicator moving along a first path of travel on the display simulating the movement of a first cycle therealong, and displaying a second user indicator moving along a second path of travel on the display simulating the movement of a second cycle therealong, the first and second paths of travel being displayed on the display to simulate the travel of two cycles racing each other; and a display control measuring the exercise efforts of the first and second users applied to the first and second exercise cycles and determining the cumulative exercise efforts of the first and second users, the display control determining when the cumulative exercise effort of one of the first and second users is within a preselected range less than the cumulative exercise effort of the other of the first and second users, and while the cumulative exercise effort of the one user remains within the preselected range and in response thereto, adjusting upward the cumulative exercise effort of the one user by a predetermined amount, the display control controlling movement of the first and second user indicators along the first and second paths of travel of the display, with the displayed movement of the first user indicator along the first path of travel being indicative of the first user adjusted cumulative exercise effort, and with the displayed movement of the second user indicator along the second path of travel being indicative of the second user adjusted cumulative exercise effort, the display control thereby simulating the one user drafting behind the other user.

28. An exercise system, comprising:

a first exercise cycle for a first user to apply a first user exercise effort;

a second exercise cycle for a second user to apply a second exercise effort;

a display control measuring the exercise efforts of the first and second users applied to the first and second exercise cycles and determining the cumulative exercise efforts of the first and second users, the display control determining when the cumulative exercise effort of one of the first and second users is within a preselected range less than the cumulative exercise effort of the other of the first and second users, and while the cumulative exercise effort of the one user remains within the preselected range and in response thereto, adjusting upward the cumulative exercise effort of the one user by a predetermined amount; and a display displaying an indication of the relative adjusted cumulative exercise efforts of the first and second users.

29. An exercise system, comprising:

a first exercise apparatus for a first user to apply a first user exercise force at a first user exercise speed;

a second exercise apparatus for a second user to apply a second exercise force at a second exercise speed;

a display displaying a first user indicator moving along a first path of travel on the display simulating the movement of the first user therealong, and displaying a second user indicator moving along a second path of travel on the display simulating the movement of the second user therealong, the first and second paths of travel being displayed on the display to simulate the travel of the two users racing each other; and a display control measuring the exercise speed of the first and second users applied to the first and second exercise apparatus, determining the cumulative exercise efforts of the first and second users applied to the first and second exercise apparatus, and determining when the cumulative exercise effort of one of the first and second users is within a preselected range less than the cumulative exercise effort of the other of the first and second users, and while the cumulative exercise effort of the one user remains within the preselected range and in response thereto, adjusting the cumulative exercise effort of the one user relative to the cumulative exercise effort of the other user by a predetermined amount, the display control controlling movement of the first and second indicators along the first and second paths of travel of the display, with the displayed movement of the first user indicator along the first path of travel being indicative of the first user adjusted cumulative exercise effort, and with the displayed movement of the second user indicator along the second path of travel being indicative of the second user adjusted cumulative exercise effort, whereby the first and second user indicators are caused to travel along the first and second paths of travel at rates corresponding to the adjusted exercise efforts of the first and second user, thereby giving the one user an advantage over the other user.

30. An exercise system, comprising:

a first exercise apparatus for a first user to apply a first user exercise force at a first user exercise speed:

a second exercise apparatus for a second user to apply a second exercise force at a second exercise speed;

a display control measuring the exercise speed of the first and second users applied to the first and second exercise apparatus, determining the cumulative exercise efforts of the first and second users applied to the first and second exercise apparatus, and determining when the cumulative exercise effort of one of the first and second users is within a preselected range less than the cumulative exercise effort of the other of the first and second users, and while the cumulative exercise effort of the one user remains within the preselected range and in response thereto, adjusting the cumulative exercise effort of the one user relative to the cumulative exercise effort of the other user to give the one user an advantage over the other user; and a display displaying an indication of the relative adjusted cumulative exercise efforts of the first and second users.

31. An exercise system, comprising:

a first exercise apparatus for a first user to apply a first user exercise effort;

a second exercise apparatus for a second user to apply a second exercise effort;

a display displaying a first user indicator moving along a first path of travel on the display simulating the movement of the first user therealong, and displaying a second user indicator moving along a second path of travel on the display simulating the movement of the second user therealong, the first and second paths of travel being displayed on the display to simulate the travel of the two users racing each other; and a display control measuring the exercise efforts of the first and second users applied to the first and second exercise apparatus and determining the cumulative exercise efforts of the first and second users, the display control determining when the cumulative exercise effort of one of the first and second users is within a preselected range less than the cumulative exercise effort of the other of the first and second users, and while the cumulative exercise effort of the one user remains within the preselected range and in response thereto, adjusting the cumulative exercise effort of the one user relative to the cumulative exercise effort of the other user by a predetermined amount, the display control controlling movement of the first and second user indicators along the first and second paths of travel of the display, with the displayed movement of the first user indicator along the first path of travel being indicative of the first user adjusted cumulative exercise effort, and with the displayed movement of the second user indicator along the second path of travel being indicative of the second user adjusted cumulative exercise effort, the display control thereby giving the one user an advantage over the other user.

32. The exercise system of claim 31 wherein the display includes a first display mounted in association with the first exercise apparatus for viewing by the first user and a second display mounted in association with the second exercise apparatus for viewing by the second user, and the display control includes a first display control controlling movement of the first and second user indicators on the first display and a second display control controlling movement of the first and second indicators on the second display.

33. The exercise system of claim 32 wherein the first and second displays each define the first path of travel by a displayed first lane with the first user indicator moving along in the first lane and the second path of travel by a displayed second lane with the second user indicator moving along in the second lane.

34. The exercise system of claim 33 wherein the first lane displayed on the first display is marked to identify to the first user the first lane as having the first user indicator, and the second lane displayed on the second display is marked to identify to the second user the second line as having the second user indicator.

35. The exercise system of claim 33 wherein the first and second lanes each extend between spaced apart first and second ends, and each has a first path portion along which the corresponding first or second user indicator travels from the first end to the second end and a second path portion along which the corresponding first or second user indicator travels from the second end to the first end.

36. The exercise system of claim 31 wherein the display further displays a statement of which of the first or second users is the one user with an adjusted cumulative exercise effort within the preselected range during the time when the adjusted cumulative exercise effort remain with the preselected range.

37. The exercise system of claim 31 wherein the display further displays a statement of which of the first or second users had the greatest adjusted cumulative exercise effort and which has the lesser adjusted cumulative exercise effort.

38. The exercise system of claim 31 wherein the display control adjusts the cumulative exercise effort of the one user by a first predetermined amount if within a first subrange of values of the preselected range and by a second predetermined amount less than the first predetermined amount if within a second subrange of values of the preselected range, with the second subrange of values being greater in numerical value than the first subrange of values, whereby the one user receives a greater adjustment of the cumulative exercise effort when within the preselected range if within the first subrange of values corresponding to a smaller difference between the cumulative exercise efforts of the first and second users.

39. The exercise system of claim 31 further including a user activated start selector, and wherein the display control determines the cumulative exercise efforts of the first and second users commencing upon user activation of the start selector.

40. The exercise system of claim 3 1 wherein each of the first and second exercise apparatus includes an input member engageable by at least one limb of the user, a resistance member applying a variable resistance to the input member to resist movement of the input member and a resistance control adjustably controlling the resistance of the resistance member, and wherein the resistance control reduces the resistance the resistance member applies to the input member of the corresponding first or second exercise apparatus of the one user while the cumulative exercise effort of the one user is being adjusted upward.

41. The exercise system of claim 31 wherein the display control determines the cumulative exercise effort of the first and second users during an exercise period by determining a current exercise effort of the corresponding first or second user during a current time interval and summing the determined current exercise effort with the previously determined cumulative exercise efforts during the exercise period.

42. The exercise system of claim 41 wherein the display control adjusts upward the cumulative exercise effort of the one user by adjusting upward the determined current exercise effort.

43. An exercise system, comprising:

a first exercise apparatus for a first user to apply a first user exercise effort;

a second exercise apparatus for a second user to apply a second exercise effort;

a display control measuring the exercise efforts of the first and second users applied to the first and second exercise apparatus and determining the cumulative exercise efforts of the first and second users, the display control determining when the cumulative exercise effort of one of the first and second users is within a preselected range less than the cumulative exercise effort of the other of the first and second users, and while the cumulative exercise effort of the one user remains within the preselected range and in response thereto, adjusting the cumulative exercise effort of the one user relative to the cumulative exercise effort of the other user to give the one user an advantage over the other user; and a display displaying an indication of the relative adjusted cumulative exercise efforts of the first and second users.

44. The exercise system of claim 1 wherein the display includes a first display mounted in association with the first exercise apparatus for viewing by the first user and a second display mounted in association with the second exercise apparatus for viewing by the second user, and the display control includes a first display control controlling movement of the first and second user indicators on the first display and a second display control controlling movement of the first and second indicators on the second display.

45. The exercise system of claim 43 wherein the display further displays a numerical indication of the adjusted cumulative exercise efforts of the first and second users.

46. The exercise system of claim 43 wherein the display further displays a statement of which of the first or second users is the one user with an adjusted cumulative exercise effort within the preselected range during the time when the adjusted cumulative exercise effort remains within the preselected range.

47. The exercise system of claim 43 wherein the display further displays a statement of which of the first or second users has the greatest adjusted cumulative exercise effort and which has the lesser adjusted cumulative exercise effort.

48. The exercise system of claim 43 wherein the display control adjusts the cumulative exercise effort of the one user relative to the other user by a first predetermined amount if within a first subrange of values of the preselected range and by a second predetermined amount less than the first predetermined amount if within a second subrange of values of the preselected range.

49. The apparatus of claim 43 wherein the display control converts the adjusted cumulative exercise effort of the first and second users into equivalent positions of the first user relative to the second user along a path of travel, and the display displays an indicator for each of the first and second users positioned along the path of travel at its equivalent positions.

50. The exercise system of claim 43, further including a user activated start selector, and wherein the display control determines the cumulative exercise efforts of the first and second users commencing upon user activation of the start selector.

51. The exercise system of claim 1 wherein each of the first and second exercise apparatus includes an input member engageable by at least one limb of the user, a resistance member applying a variable resistance to the input member to resist movement of the input member and a resistance control adjustably controlling the resistance of the resistance member, and wherein the resistance control reduces the resistance the resistance member applies to the input member of the corresponding first or second exercise apparatus of the one user while the cumulative exercise effort of the one user is being adjusted relative to the other user.

52. The exercise system of claim 43 wherein the display control determines the cumulative exercise effort of the first and second users during an exercise period by determining a current exercise effort of the corresponding first or second user during a current time interval and summing the determined current exercise effort with the previously determined cumulative exercise efforts during the exercise period.

53. The exercise system of claim 52 wherein the display control adjusts the cumulative exercise effort of the one user relative to the other user by adjusting upward the determined current exercise effort of the one user.

54. An exercise system, comprising:

a first exercise apparatus for a first user to apply a first user exercise force at a first user exercise speed;

a second exercise apparatus for a second user to apply a second exercise force at second exercise speed;

a third exercise apparatus for a third user to apply a third exercise force at a third exercise speed;

a display displaying a first user indicator moving along a first path of travel on the display simulating the movement of the first user therealong, displaying a second user indicator moving along a second path of travel on the display simulating the movement of the second user therealong, and displaying a third user indicator moving along a third path of travel on the display simulating the movement of the third user therealong, the first, second and third paths of travel being displayed on the display to simulate the travel of the three users racing each other; and a display control measuring the exercise speed of the first, second and third users applied to the first, second and third exercise apparatus, determining the cumulative exercise efforts of the first, second and third users applied to the first, second and third exercise apparatus, determining a lead user based on which of the first, second or third users has the greatest cumulative exercise effort, and determining when the cumulative exercise effort of particular ones of the first, second and third users are within a preselected range less than the cumulative exercise effort of the lead user, and while the cumulative exercise effort of the particular users remains within the preselected range and in response thereto, adjusting upward the cumulative exercise effort of the particular users by predetermined amounts, the display control controlling movement of the first, second and third indicators along the first, second and third paths of travel of the display, with the displayed movement of the first user indicator along the first path of travel being indicative of the first user adjusted cumulative exercise effort, with the displayed movement of the second user indicator along the second path of travel being indicative of the second user adjusted cumulative exercise effort, and with the displayed movement of the third user indicator along the third path of travel being indicative of the third user adjusted cumulative exercise effort, whereby the corresponding first, second or third user indicator of the particular users are caused to travel along the corresponding first, second or third path of travel at a rate corresponding to the upwardly adjusted exercise effort of the particular users, thereby giving the particular users an advantage over the lead user.

55. The exercise system of claim 54, further including the display control determining which of the particular ones of the first, second and third users has a cumulative exercise effort closest to and next closest to the cumulative exercise effort of the lead user, and adjusting upward the cumulative exercise effort of the closest user by a first predetermined amount, and adjusting upward the cumulative exercise effort of the next closest user by a second predetermined amount, with the second predetermined amount being greater than the first predetermined amount, whereby the closest user to the lead user gets a first level of benefit from being behind the lead user and the next closest user to the lead user gets an increased second level of benefit from being behind both the lead user and the closest user.

56. An exercise system, comprising:

a first exercise apparatus for a first user to apply a first user exercise force at a first user exercise speed;

a second exercise apparatus for a second user to apply a second exercise force at a second exercise speed;

a third exercise apparatus for a third user to apply a third exercise force at a third exercise speed;

a display control measuring the exercise speed of the first, second and third users applied to the first, second and third exercise apparatus, determining the cumulative exercise efforts of the first, second and third users applied to the first, second and third exercise apparatus, determining a lead user based on which of the first, second or third users has the greatest cumulative exercise effort, and determining when the cumulative exercise effort of particular ones of the first, second and third users are within a preselected range less than the cumulative exercise effort of the lead user, and while the cumulative exercise effort of the particular users remains within the preselected range, and in response thereto, adjusting the cumulative exercise effort of the particular users relative to the cumulative exercise effort of the lead user to give the particular users an advantage over the lead user; and a display displaying an indication of the relative adjusted cumulative exercise efforts of the first, second and third users.

57. The exercise system of claim 56, further including the display control determining which of the particular ones of the first, second and third users has a cumulative exercise effort closest to and next closest to the cumulative exercise effort of the lead user, and adjusting upward the cumulative exercise effort of the closest user by a first predetermined amount, and adjusting upward the cumulative exercise effort of the next closest user by a second predetermined amount, with the second predetermined amount being greater than the first predetermined amount, whereby the closest user to the lead user gets a first level of benefit from being behind the lead user and the next closest user to the lead user gets an increased second level of benefit from being behind both the lead user and the closest user.

58. An exercise system, comprising:

a first exercise apparatus for a first user to apply a first user exercise effort;

a second exercise apparatus for a second user to apply a second exercise effort;

a third exercise apparatus for a third user to apply a third exercise effort;

a display displaying a first user indicator moving along a first path of travel on the display simulating the movement of the first user therealong, displaying a second user indicator moving along a second path of travel on the display simulating the movement of the second user therealong, and displaying a third user indicator moving along a third path of travel on the display simulating the movement of the third user therealong, the first, second and third paths of travel being displayed on the display to simulate the travel of the three users racing each other; and a display control measuring the exercise efforts of the first, second and third users applied to the first, second and third exercise apparatus and determining the cumulative exercise efforts of the first, second and third users, the display control determining a lead user based on which of the first, second or third users has the greatest cumulative exercise effort, and determining when the cumulative exercise effort of particular ones of the first, second and third users are within a preselected range less than the cumulative exercise effort of the lead user, and while the cumulative exercise effort of the particular users remains within the preselected range and in response thereto, adjusting the cumulative exercise effort of the particular users relative to the cumulative exercise effort of the lead user by predetermined amounts, the display control controlling movement of the first, second and third user indicators along the first, second and third paths of travel of the display, with the displayed movement of the first user indicator along the first path of travel being indicative of the first user adjusted cumulative exercise effort, with the displayed movement of the second user indicator along the second path of travel being indicative of the second user adjusted cumulative exercise effort, and with the displayed movement of the third user indicator along the third path of travel being indicative of the third user adjusted cumulative exercise effort, the display control thereby giving the particular users an advantage over the lead user.

59. The exercise system of claim 58, further including the display control determining which of the particular ones of the first, second and third users has a cumulative exercise effort closest to and next closest to the cumulative exercise effort of the lead user, and adjusting upward the cumulative exercise effort of the closest user by a first predetermined amount, and adjusted upward the cumulative exercise effort of the next closest user by a second predetermined amount, with the second predetermined amount being greater than the first predetermined amount, whereby the closest user to the lead user gets a first level of benefit from being behind the lead user and the next closest user to the lead user gets and increased second level of benefit from being behind both the lead user and the closest user.

60. An exercise system, comprising:

a first exercise apparatus for a first user to apply a first user exercise effort;

a second exercise apparatus for a second user to apply a second exercise effort;

a third exercise apparatus for a third user to apply a third exercise effort;

a display control measuring the exercise efforts of the first, second and third users applied to the first, second and third exercise apparatus and determining the cumulative exercise efforts of the first, second and third users, the display control determining a lead user based on which of the first, second or third users has the greatest cumulative exercise effort, and determining when the cumulative exercise effort of particular ones of the first, second and third users are within a preselected range less than the cumulative exercise effort of the lead user, and while the cumulative exercise effort of the particular users remains within the preselected range and in response thereto, adjusting the cumulative exercise effort of the particular users relative to the cumulative exercise effort of the lead user to give the particular users an advantage over the lead user; and a display displaying an indication of the relative adjusted cumulative exercise efforts of the first, second and third users.

61. The exercise system of claim 60, further including the display control determining which of the particular ones of the first, second and third users has a cumulative exercise effort closest to and next closest to the cumulative exercise effort of the lead user, and adjusting upward the cumulative exercise effort of the closest user by a first predetermined amount, and adjusting upward the cumulative exercise effort of the next closest user by a second predetermined amount, with the second predetermined amount being greater than the first predetermined amount, whereby the closest user to the lead user gets a first level of benefit from being behind the lead user and the next closest user to the lead user gets an increased second level of benefit from being behind both the lead user and the closest user.

\* \* \* \* \*

UNITED STATES PATENT AND TRADEMARK OFFICE
CERTIFICATE OF CORRECTION

PATENT NO. : 5,547,439
DATED : August 20, 1996
INVENTOR(S) : R. Lee Rawls et al.

It is certified that error appears in the above-indentified patent and that said Letters Patent is hereby corrected as shown below:

In column 12, claim 4, line 33, please delete "identified" and insert therefor --identify--.

Signed and Sealed this

Eighteenth Day of February, 1997

Attest:

BRUCE LEHMAN

*Attesting Officer*   *Commissioner of Patents and Trademarks*